US009771543B2

(12) United States Patent
Bergen-Brenkman et al.

(10) Patent No.: US 9,771,543 B2
(45) Date of Patent: Sep. 26, 2017

(54) PROCESS FOR PRODUCING MONOBRANCHED FATTY ACIDS OR ALKYL ESTERS THEREOF

(71) Applicant: CRODA INTERNATIONAL PLC, Yorkshire (GB)

(72) Inventors: Tanja Van Bergen-Brenkman, Gouda (NL); Negar Rashidi, Rijswijk (NL); Bastiaan Wels, Houten (NL)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 14/438,051

(22) PCT Filed: Oct. 7, 2013

(86) PCT No.: PCT/GB2013/052603
§ 371 (c)(1),
(2) Date: Apr. 23, 2015

(87) PCT Pub. No.: WO2014/064418
PCT Pub. Date: May 1, 2014

(65) Prior Publication Data
US 2015/0291912 A1  Oct. 15, 2015

(30) Foreign Application Priority Data
Oct. 25, 2012  (GB) .................................. 1219224.1

(51) Int. Cl.
| | | |
|---|---|---|
| C11C 3/14 | (2006.01) | |
| C07C 51/353 | (2006.01) | |
| C07C 51/36 | (2006.01) | |
| C11C 1/10 | (2006.01) | |
| C11C 3/12 | (2006.01) | |
| B01J 29/65 | (2006.01) | |
| C11C 1/00 | (2006.01) | |

(52) U.S. Cl.
CPC ............... *C11C 3/14* (2013.01); *B01J 29/65* (2013.01); *C07C 51/353* (2013.01); *C07C 51/36* (2013.01); *C11C 1/002* (2013.01); *C11C 1/10* (2013.01); *C11C 3/12* (2013.01); *C11C 3/123* (2013.01)

(58) Field of Classification Search
CPC ....................................................... C11B 3/14
See application file for complete search history.

(56) References Cited

U.S. PATENT DOCUMENTS

| | | | |
|---|---|---|---|
| 3,351,566 A | 11/1967 | Taylor | |
| 4,490,480 A | 12/1984 | Lok | |
| 5,481,025 A | 1/1996 | Laufenberg | |
| 5,677,473 A * | 10/1997 | Tomifuji | ............... C07C 51/353 502/77 |
| 6,455,716 B2 | 9/2002 | Kenneally | |
| 6,846,772 B2 | 1/2005 | Lok | |
| 6,946,567 B2 * | 9/2005 | Zhang | ..................... B01J 29/06 502/60 |
| 2004/0204598 A1 | 10/2004 | Zhang | |
| 2008/0045731 A1 * | 2/2008 | Zhang | ..................... C11C 3/003 554/124 |
| 2015/0005211 A1 * | 1/2015 | Townsend | ............. C07C 233/05 508/459 |

FOREIGN PATENT DOCUMENTS

| | | |
|---|---|---|
| CN | 1498200 | 5/2004 |
| EP | 0167201 | 1/1986 |
| EP | 0168091 | 1/1986 |
| EP | 0683150 | 11/1995 |
| EP | 0774451 | 5/1997 |
| WO | 9106367 | 5/1991 |
| WO | 0166507 | 9/2001 |
| WO | 03006157 | 1/2003 |
| WO | 2010149952 | 12/2010 |
| WO | 2011136903 | 11/2011 |
| WO | 2012146909 | 11/2012 |

OTHER PUBLICATIONS

Zhang, Z. C., et al., New Process for the Production of Branched-Chain Fatty acids, 2004, Journal of Surfactants and Detergents, vol. 7, No. 3, pp. 211-215.*
Bonilla, A., et al., "Desilication of ferrierite zeolite for porosity generation and improved effectiveness in polyethylene pyrolysis," 2009, pp. 170-180, vol. 265, Journal of Catalysis.
International Search Report for International Application No. PCT/GB2013/052603 dated Jun. 20, 2014.
Kwak, B.S., et al., "Skeletal isomerization of 1-butene over surface modified ferrierite catalysts," 1998, pp. 125-129, vol. 53, Catalysis Letters.
Ngo, H.L. et al., "Zeolite-catalyzed isomerization of oleic acid to branched-chain isomers," 2007, pp. 214-224, vol. 108, European Journal of Lipid Science and Technology.
Park, H.J., et al., "Catalytic degradation of polyethylene over ferrierite," 2008, pp. 1-9, vol. 0, No. 0, Research on Chemical Intermediates.
Pinar, A., et al., "Control of acid sites location in zeolite ferrierite via an organic template-driven approach: an efficient tuning of catalytic activity," Institute of Catalysis and Petroleum Chemistry (CSIC), Madrid, Spain.
Roman-Leshkov, Y., et al., "Impact of controlling the site distribution of A atoms on catalytic properties in ferrierite-type zeolites," 2011, pp. 1096-1102, vol. 115, No. 4, Journal of Physical Chemistry C.
Sivasanker, S., et al., "Surface passivation and shape selectivity in hydrocracking over ZSM-5," 1989, pp. 49-52, vol. 3, Catalysis Letters.

(Continued)

*Primary Examiner* — Yate K Cutliff
(74) *Attorney, Agent, or Firm* — RatnerPrestia

(57) ABSTRACT

A process for producing a composition having a ratio by weight of $C_{10}$-$C_{26}$ monobranched fatty acids or alkyl esters thereof to $C_{10}$-$C_{26}$ polybranched fatty acids or alkyl esters thereof of greater than 6 using a zeolite, preferably ferrierite, isomerization catalyst. The zeolite catalyst is preferably the only isomerization catalyst used. The zeolite catalyst can be reused many times after simple separation from the reaction products without having to be regenerated.

16 Claims, No Drawings

(56) References Cited

OTHER PUBLICATIONS

First Chinese Office Action dated May 4, 2016 in Chinese Application No. 201380055667.5.

* cited by examiner

US 9,771,543 B2

PROCESS FOR PRODUCING MONOBRANCHED FATTY ACIDS OR ALKYL ESTERS THEREOF

CROSS REFERENCE TO RELATED APPLICATIONS

This application is the U.S. National Phase application of PCT International Application No. PCT/GB2013/052603, filed Oct. 7, 2013, and claims priority of GB Patent Application no. 1219224.1, filed Oct. 25, 2012, the disclosures of which are incorporated herein by reference in their entireties for all purposes.

FIELD OF INVENTION

The present invention relates to a process for producing highly monobranched fatty acids or alkyl esters thereof, and in particular a composition containing a high concentration of monobranched fatty acids and a low concentration of polybranched fatty acids.

BACKGROUND

Fatty acids are versatile building blocks used in many parts of the chemical industry, in applications ranging from lubricants, polymers, and solvents to cosmetics and health care. Fatty acids are generally obtained by the hydrolysis of triglycerides of vegetable or animal origin. Naturally occurring triglycerides are esters of glycerol and generally straight chain, even numbered carboxylic acids, ranging from 10 to 24 carbon atoms. Most common are fatty acids having 12, 14, 16 or 18 carbon atoms. The fatty acids can be either saturated or contain one or more unsaturated carbon bonds.

Straight chain saturated fatty acids having 10 or more carbon atoms are solid at room temperature, which makes them difficult to process in a number of applications. Unsaturated long chain fatty acids, e.g. oleic acid, are liquid at room temperature, and so are easy to process, but are unstable because of the existence of one or more double bonds. Branched fatty acids can mimic the properties of the straight chain unsaturated fatty acids in many respects. However, they do not have the disadvantage of being unstable. Thus, branched fatty acids are, for many applications, more desirable than straight chain fatty acids. The branched fatty acids have alkyl side groups which are generally short, e.g. methyl, ethyl or propyl, and can be attached to the carbon chain backbone at any position.

Commercially available branched fatty acids, such as isostearic acid, are obtained as a by-product of the catalytic or thermal dimerisation of unsaturated straight chain fatty acids. Isostearic acid is produced by heating oleic acid in the presence of catalyst, generally clay, to produce dimer, trimer and higher oligomer acids. But instead of polymerising, a portion of the oleic acid rearranges to give a branched, monomeric fatty acid which can be isolated by distillation and hydrogenated. This saturated branched monomeric fatty acid is a mixture of various linear and mainly branched, both monobranched and polybranched, saturated acids which is known as isostearic acid.

Isostearic acid exhibits better stability to oxidation than oleic acid, and is a very useful product which is sold into a wide range of application areas such as lubricant esters, and cosmetic applications. Isostearic acid is also used to make isostearyl alcohol.

The dimerisation process only produces about 20 to 40% by weight of isostearic acid, and thus there is a need for a more efficient process. A further disadvantage, which increases the cost of the process, is that the clay catalyst cannot be reused.

EP-0683150 describes an alternative process for producing branched fatty acids by using a zeolite catalyst which has a linear pore structure. This process has a much higher selectivity towards monomeric than dimeric or oligomeric products.

WO-2011136903 is directed to a process for producing branched fatty acids by using a combination of a zeolite catalyst and a sterically hindered Lewis base which has an even higher selectivity towards monomeric than dimeric products.

We have discovered that monobranched fatty acids can have significant advantages over polybranched fatty acids. The aforementioned prior art documents are silent with regards to monobranched and polybranched fatty acids. These prior art documents do not disclose that highly monobranched fatty acids can be produced. Thus, there is a need for a process for producing highly monobranched fatty acids, i.e. a composition containing a high concentration of monobranched fatty acids and a low concentration of polybranched fatty acids.

SUMMARY OF THE INVENTION

We have now discovered a process for producing monobranched fatty acids which reduces or substantially overcomes at least one of the aforementioned problems.

Accordingly, the present invention provides a process for producing monobranched fatty acids or alkyl esters thereof which comprises;
 (i) isomerising unsaturated $C_{10}$-$C_{26}$ fatty acids or alkyl esters thereof in the presence of a catalyst comprising zeolite,
 (ii) optionally removing polymeric fatty acids,
 (iii) optionally hydrogenating the reaction product of step (i) or (ii), and
 (iv) obtaining a composition from the reaction product of step (i), (ii) or (iii) having a ratio by weight of $C_{10}$-$C_{26}$ monobranched fatty acids or alkyl esters thereof to $C_{10}$-$C_{26}$ polybranched fatty acids or alkyl esters thereof of greater than 6.

The invention also provides the use of zeolite as a catalyst in the isomerisation of unsaturated $C_{10}$-$C_{26}$ fatty acids or alkyl esters thereof to produce a composition having a ratio by weight of $C_{10}$-$C_{26}$ monobranched fatty acids or alkyl esters thereof to $C_{10}$-$C_{26}$ polybranched fatty acids or alkyl esters thereof of greater than 6.

The invention further provides a process for producing monobranched fatty acids or alkyl esters thereof which comprises;
 (A) (i) isomerising unsaturated $C_{10}$-$C_{26}$ fatty acids or alkyl esters thereof in the presence of a catalyst comprising zeolite,
  (ii) separating the reaction product of step (i) from the used zeolite,
  (iii) optionally removing polymeric fatty acids,
  (iv) optionally hydrogenating the reaction product of step (ii) or (iii),
  (v) obtaining a composition from the reaction product of step (ii), (iii) or (iv) having a ratio by weight of $C_{10}$-$C_{26}$ monobranched fatty acids or alkyl esters thereof to $C_{10}$-$C_{26}$ polybranched fatty acids or alkyl esters thereof of greater than 6, and (B) wherein the process steps (A)(i) to (v) are repeated more than once using zeolite comprising used zeolite which has been obtained from step (A)(ii) of the previous reaction cycle.

The invention still further provides the reuse of a zeolite catalyst to obtain a steady state process for producing a composition having a ratio by weight of $C_{10}$-$C_{26}$ monobranched fatty acids or alkyl esters thereof to $C_{10}$-$C_{26}$ polybranched fatty acids or alkyl esters thereof of greater than 6.

DETAILED DESCRIPTION OF THE INVENTION

The raw materials for the unsaturated fatty acids or alkyl esters thereof used in the present invention are preferably naturally occurring materials such as triglyceride oils and can be of animal (e.g. tallow), or preferably of vegetable origin. Suitable fatty acids include sunflower fatty acids, soybean fatty acids, olive fatty acids, rapeseed fatty acids, linseed fatty acids, cottonseed fatty acids, safflower fatty acids, tall oil fatty acids and tallow olein. Relatively pure unsaturated fatty acids such as oleic acid, linoleic acid, linolenic acid, palmitoleic acid, erucic acid, and elaidic acid may be isolated and used, or relatively crude unsaturated fatty acid mixtures employed. The unsaturated fatty acid component may comprise high oleic sunflower fatty acid. The unsaturated fatty acid component may be partially hydrogenated. For example, the unsaturated fatty acid component may comprise partially hydrogenated olive oil or olive fatty acid.

References to features of the invention herein are applicable to the process and/or use of the invention. References to fatty acids described herein also include the alkyl esters thereof. Thus, alkyl esters of the unsaturated fatty acids herein described having a total carbon number of 10 to 26 may be used as the starting material. Although the alkyl moiety may be up to half of the total carbon number, normally it will be 1 to 3, preferably 1 carbon atom(s). Specific examples of alkyl esters include methyl esters, ethyl esters and propyl esters of unsaturated fatty acids, with methyl esters being preferred.

When a mixture of alkyl esters is used as the starting material, the mixture contains at least one alkyl ester of the herein described unsaturated fatty acids.

Specifically, it is a mixture of one or more alkyl esters of these unsaturated fatty acids, or a mixture containing at least one alkyl ester of these unsaturated fatty acids and saturated fatty acids. In the case of a mixture, the content of alkyl esters of the herein described unsaturated fatty acids is preferably greater than 50% by weight, more preferably greater than 80% by weight, and especially greater than 90% by weight.

The unsaturated fatty acids starting material suitably comprises $C_{12}$-$C_{24}$ fatty acids, preferably $C_{14}$-$C_{22}$ fatty acids, more preferably $C_{16}$-$C_{22}$ fatty acids, particularly $C_{18}$ or $C_{22}$ fatty acids, and especially $C_{18}$ fatty acids. The fatty acids starting material suitably comprises greater than 70%, preferably greater than 80%, more preferably greater than 90%, particularly greater than 95%, and especially greater than 97% by weight of fatty acids falling within the aforementioned carbon chain ranges or number, based on the total weight of fatty acids present.

The unsaturated fatty acids starting material suitably comprises (i) greater than 70%, preferably greater than 75%, more preferably in the range from 80 to 99%, particularly 85 to 97%, and especially 90 to 95% by weight of unsaturated fatty acids; and/or (ii) less than 30%, preferably less than 25%, more preferably in the range from 1 to 20%, particularly 3 to 15%, and especially 5 to 10% by weight of saturated fatty acids, both based on the total weight of fatty acids present.

The unsaturated fatty acid component comprises at least one ethylenic double bond, but may comprise two or even three double bonds. The unsaturated fatty acid component suitably comprises (i) greater than 50%, preferably greater than 60%, more preferably in the range from 80 to 100%, particularly 85 to 98%, and especially 90 to 95%, by weight of fatty acids having one double bond; and/or (ii) less than 50%, preferably less than 40%, more preferably in the range from 0 to 20%, particularly 2 to 15%, and especially 5 to 10% by weight of fatty acids having 2 or 3, preferably 2, double bonds, both based on the total weight of unsaturated fatty acids present.

The zeolite catalyst is suitably used at a concentration of less than 10%, preferably less than 5%, more preferably in the range from 0.1 to 2%, particularly 0.3 to 1.5%, and especially 0.5 to 1% by weight based on the weight of fatty acids starting material.

One advantage of the present invention is that the zeolite can be directly reused many times, without being subjected to regeneration. By "reused" is meant used again as a catalyst after one or more reaction cycles without being subjected to regeneration. By "regeneration" is meant isolation of the zeolite followed by treatments such as washing with solvent, and/or heating, for example, in air or an inert atmosphere or acid solution, and drying.

In a preferred embodiment of the present invention, the zeolite allows multiple reuse after simple separation from the reaction products, e.g. by filtration or centrifugation. Surprisingly little loss of the zeolite activity occurs on reuse. Thus, the zeolite may be suitably reused once, preferably 2 or more times, more preferably 3 or more times, especially 4 or more times, and particularly 5 or more times. We have surprisingly found that after 2 reuses of the zeolite (three reaction cycles) a steady state can be effectively achieved which enables almost infinite or continuous reuse, i.e. can be used in a batch or a continuous process. The steady state is shown by the retention of catalyst activity.

Thus, the zeolite catalyst preferably retains at least 90%, more preferably at least 95%, particularly at least 97%, and especially at least 99% of its activity after the third, preferably the fourth, more preferably the fifth, particularly the sixth, and especially after further subsequent reuses.

Zeolite activity is determined as described herein. Loss of activity of the reused zeolite is measured as the increase in time required to achieve the same degree of conversion as obtained for the second reuse of the zeolite. Zeolite activity is expressed as the percentage retention of activity. 100% retention of activity means that the same degree of conversion occurred during the same time period as for the second reuse of the zeolite.

In one embodiment, the zeolite is reused without the addition of any, or significant quantities, of fresh (unused) or regenerated zeolite. Thus, after the first reaction cycle, the zeolite catalyst employed suitably comprises (i) greater than 95%, preferably greater than 96%, more preferably greater than 97%, particularly greater than 98%, and especially greater than 99% by weight of used catalyst; and/or (ii) less than 5%, preferably less than 4%, more preferably less than 3%, particularly less than 2%, and especially less than 1% by weight of fresh or regenerated zeolite, both based on the total (dry) weight of zeolite present.

In normal processing, some of the zeolite catalyst will be lost during recovery and therefore some fresh or regenerated zeolite will need to be added to the reused catalyst to maintain the zeolite concentration. Thus, after the first reaction cycle, the zeolite catalyst employed suitably comprises (i) 95% or less, preferably 90% or less, more preferably in the range from 70 to 86%, particularly 75 to 84%, and especially 78 to 82% by weight of used catalyst; and/or (ii) 5% or greater, preferably 10% or greater, more preferably in the range from 14 to 30%, particularly 16 to 25%, and especially 18 to 22% by weight of fresh or regenerated zeolite, both based on the total (dry) weight of zeolite present.

In one embodiment, the isomerisation reaction suitably occurs over a time period of 0.5 to 16 hours, preferably 1 to 12 hours, more preferably 2 to 10 hours, particularly 3 to 8 hours, and especially 4 to 6 hours.

The isomerization reaction is suitably carried out at 150 to 350° C., preferably 200 to 300° C., more preferably 225 to 280° C., particularly 250 to 270° C., and especially 255 to 265° C. The reaction may be carried out in a closed system, such as an autoclave, where the system can be pressurized. A suitable pressure is 2 to 50 kgf/cm$^2$. The reaction mixture may be flushed out, and pressurized, with a gas such as nitrogen or hydrogen, preferably nitrogen. The use of a closed system will prevent vaporization of water, alcohols and any other low boiling substances in the system, including any contained in the catalyst.

The zeolite isomerisation catalyst used in the present invention is a crystalline aluminosilicate, which preferably has the general formula $M^{n+}{}_{x/n}[(AlO_2)_x(SiO_2)_{y(y>x)}] \cdot zH_2O$, where M is a metal cation of groups IA (including hydrogen) or IIA, and n is the valency of the metal. The zeolite suitably comprises a microporous network of $SiO_4$ and $AlO_4$ tetrahedra linked together via shared oxygen atoms. The aluminium preferably has a 3+ valency resulting in an excess negative charge on the $AlO_4$ tetrahedra, which can be compensated by $H^+$ or other cations, e.g. $Na^+$, $NH_4^+$, $Ca^{2+}$. When M is hydrogen, the materials are Bronsted acidic, whereas when M is, for example, caesium, the materials are basic. Upon heating, Bronsted acidic hydroxyls condense creating coordinately unsaturated Al, which acts as a Lewis acid site. The acid strength, acid site density and distribution and Bronsted versus Lewis acidity are determined by the level of framework aluminium. The ratio of silica/alumina can be varied for a given class of zeolites either by controlled calcination, with or without the presence of steam, optionally followed by extraction of the resulting extraframework aluminium, or by chemical treatment employing, for example, ammonium hexafluorosilicate. Alternatively the ratio can be controlled within limits at the manufacturing stage by variation of the reactant stoichiometry. The zeolite used in the present invention preferably has a silica/alumina ratio of the catalyst in the range from 3 to 300, more preferably 5 to 200, and particularly 10 to 100. The ratio can be easily determined by atomic absorption photometry.

In one embodiment, the zeolite catalyst has a "linear pore structure", wherein pores are formed by at least linear continuous pathways, and pore mouths at the transition between the pores and the catalyst surface. In addition, the zeolite preferably has pores which are small enough to retard dimerisation and coke formation within the pore structure or in the pore mouth, and large enough to allow diffusion of branched chain fatty acids or esters thereof out of the pores and pore mouths. The mean pore size of the largest channels of the zeolite is preferably in the range from 4 to 9 Angstrom, and more preferably 4 to 7 Angstrom. The zeolite preferably does not have additional larger cavities. Such zeolites belong to the "medium or intermediate pore size zeolites" and examples include ferrierite, stilbite, mordenite and/or beta, L type zeolites. Ferrierite type zeolites are particularly preferred, and the use thereof can surprisingly result in the production of high concentrations of monobranched fatty acids and low concentrations of polybranched fatty acids.

In addition to pore topology, the morphology and/or crystallite size of the zeolite material may also be important. The crystallite morphology can be accurately quantified by measuring the crystallite diameter and the crystallite depth, e.g. the maximum crystallite diameter (L) and the maximum crystallite depth (D). These can be measured using a combination of scanning electron microscopy (SEM) and/or transmission electron microscopy (TEM), e.g. as described in WO 91/06367. The L/D ratio (crystallite aspect ratio) is preferably greater than 8, more preferably greater than 10, particularly in the range from 15 to 40, and especially 20 to 30.

One particularly suitable type of ferrierite zeolite comprises channels of ten-membered rings (10-MR) in one direction, and nine-or-less-membered ring intersecting channels in the other directions. In such zeolite catalysts, there are no extra cavities at the intersections. The ferrierite is characterised by a two dimensional pore system consisting of 10-MR channels parallel to [001] interconnected with 8-MR channels parallel to [010]. Additionally, small channels formed by six-membered rings are present. Both 10-MR and 8-MR channels are elliptical in shape with dimensions of 4.2×5.4 Angstroms and 3.5×4.8 Angstroms, respectively (see Meier, W M; Olson, D H; Baerlocher, Ch, Atlas of Zeolite Structure Types, 4$^{th}$ revised ed.; Elsevier; London, 1996; p 106). A particularly preferred zeolite catalyst is CP914C ($NH_4^+$ form, ex Zeolyst). The use of CP914C according to the present invention can surprisingly result in the production of very high concentrations of monobranched fatty acids and very low concentrations of polybranched fatty acids.

In addition, zeolites with structures close to the above preferred class may be converted to the desired pore structures using methods known to those skilled in the art. For example, zeolites having channels with smaller pore size can be enlarged by replacing alkali (earth) metals by hydrogen; and alternatively, zeolites with larger pore size can be reduced by substituting the alkali metals with larger ions such as larger alkaline earth metals.

Zeolites such as the above may be modified after synthesis using a variety of post treatments. Representative but not exclusive methods are passivation of the external surface by silication (e.g. by treatment with di-trimethylsilylamine (Catalysis Letters 3 (1989) 49-52) or oxalic acid (Catalysis Letters 53 (1998) 125-129)). Most suitable are methods to reduce dimer formation which deactivate the external surface (this reducing the Si/Al ratio of the zeolite surface to below 10).

Although it is preferable from the viewpoint of catalyst activity that the cation in the zeolite is a proton, a zeolite of the potassium, ammonium or similar type, may be used after being converted, either partially or completely, into the proton type by suitable methods such as ion exchange or calcination.

The zeolite described herein is preferably the only catalyst used in the isomerisation reaction, i.e. preferably a co-catalyst is not used and the isomerisation catalyst consists of zeolite, preferably ferrierite. Preferably in the process and/or use of the invention, the isomerisation catalyst consists of zeolite. Preferably in the process and/or use of the invention, the zeolite is a ferrierite.

In particular, a Lewis base is not used as a co-catalyst and/or is not present in the isomerisation reaction mixture. Preferably in the process and/or use of the invention, the isomerisation reaction mixture does not comprise a Lewis base.

If present, the Lewis base may be a sterically hindered Lewis base, i.e. of sufficient size that it cannot enter the internal pore structure of the zeolite. The Lewis base may comprise at least one heteroatom such as a nitrogen, phosphorus, oxygen or sulphur atom, more preferably a nitrogen or phosphorus atom, and particularly a phosphorus atom. The Lewis base may be an amine or phosphine, particularly an organoamine or organophosphine, and especially triphenylphosphine. Surprisingly the process according to the present invention exhibits high selectivity towards monomeric rather than dimeric or oligomeric products and/or produces a high concentration of monobranched fatty acids and a low concentration of polybranched fatty acids, in the absence of Lewis base defined herein.

The isomerisation reaction may be carried out in the presence of water or a lower alcohol. This is to suppress acid anhydride formation due to dehydration or dealcoholation of the starting material. It is preferable to add water when the starting material is unsaturated fatty acids; and an alcohol when the starting material is esters of unsaturated fatty acids.

The lower alcohol used suitably comprises 1 to 3 carbon atoms, with methanol, ethanol, and propanol being preferred. The lower alcohol preferably has the same alkyl group as that of the fatty acid ester starting material.

The composition obtained from the isomerisation reaction comprises a high concentration (suitably greater than 60 wt %, preferably greater than 65 wt %, more preferably greater than 70 wt %) of branched chain unsaturated fatty acids, or alkyl esters thereof. The composition also comprises a relatively low concentration (suitably less than 15 wt %, preferably less than 10 wt %, more preferably less than 5 wt %) of polymeric fatty acids such as dimer acid and trimer acid, and these can be removed, for example by vacuum distillation at a suitable temperature, e.g. up to 230° C. Where a hydrogenation step is employed, the polymeric fatty acids may be removed after hydrogenation.

The branched chain unsaturated fatty acids comprise a mixture of both monobranched unsaturated fatty acids and polybranched unsaturated fatty acids. The monobranched unsaturated fatty acids and polybranched unsaturated fatty acids can be converted to monobranched saturated fatty acids and polybranched saturated fatty acids by hydrogenation.

The monobranched (unsaturated and/or saturated) fatty acids comprise a single alkyl side branch, whereas the polybranched (unsaturated and/or saturated) fatty acids comprise 2 or more alkyl side branches. The alkyl side branches of the monobranched and/or polybranched fatty acids are attached directly to a carbon atom of the longest linear chain and are preferably methyl, ethyl, propyl, or mixtures thereof. In a preferred embodiment, (i) greater than 75, more preferably greater than 85, particularly in the range from 90 to 98, and especially 93 to 96 molar % of the side-branched groups are methyl groups; and/or (ii) less than 25, more preferably less than 15, particularly in the range from 2 to 10, and especially 4 to 7 molar % of the side-branched groups are ethyl and/or propyl groups.

The monobranched and/or polybranched fatty acids suitably comprise $C_{12}$-$C_{24}$, preferably $C_{14}$-$C_{22}$, more preferably $C_{16}$-$C_{22}$, particularly $C_{18}$ or $C_{22}$, and especially $C_{18}$ fatty acids. The monobranched and/or polybranched fatty acids suitably comprise greater than 70%, preferably greater than 80%, more preferably greater than 90%, particularly greater than 93%, and especially greater than 95%, by weight of fatty acids falling within the aforementioned carbon chain ranges, based on the total weight of monobranched and/or polybranched fatty acids present.

The ratio by weight of monobranched fatty acids to polybranched fatty acids in the composition obtained from the isomerisation reaction is (i) suitably greater than 8, preferably greater than 10, more preferably greater than 12, particularly greater than 14, and especially greater than 15, and/or (ii) suitably less than 100, preferably less than 50, more preferably less than 40, particularly less than 30, and especially less than 20.

The concentration of monobranched fatty acids in the composition is (i) suitably greater than or equal to 85%, preferably greater than or equal to 88%, more preferably greater than or equal to 90%, particularly greater than or equal to 92%, and especially greater than or equal to 94% by weight, and/or the concentration of polybranched fatty acids in the composition is (ii) suitably less than or equal to 15%, preferably less than or equal to 12%, more preferably less than or equal to 10%, particularly less than or equal to 8%, and especially less than or equal to 6% by weight, both based on the total weight of monobranched and polybranched fatty acids present in the composition.

The conversion rate, i.e. the % by weight of unsaturated fatty acid starting material which is reacted in the isomerisation reaction is suitably greater than 75%, preferably greater than 80%, more preferably greater than 85%, particularly in the range from 88 to 98%, and especially 90 to 95% by weight.

The zeolite catalyst can be separated from the reaction product of the isomerisation reaction, for example by filtration, preferably using a pressurized filtration unit with carton depth filter, and preferably reused as described herein.

The reaction product of the isomerisation reaction is optionally hydrogenated, for example in an autoclave by a known method, such as the method using a standard hydrogenation catalyst, particularly a metal hydrogenation catalyst. Catalysts for hydrogenation are well known and can be homogeneous or heterogeneous (e.g. present in a different phase, typically the solid phase, than the substrate). Other useful hydrogenation catalysts include nickel, copper, palladium, platinum, molybdenum, iron, ruthenium, osmium, rhodium, iridium, zinc or cobalt, and particularly zinc. Combinations of catalysts can also be used. Bimetallic catalysts can be used, for example, palladium-copper, palladium-lead, nickel-chromite.

The metal hydrogenation catalysts can be utilized with promoters that may or may not be other metals. Typical metal catalysts with promoter include, for example, nickel with sulfur or copper as promoter; copper with chromium or zinc as promoter; zinc with chromium as promoter; or palladium on carbon with silver or bismuth as promoter.

In one embodiment, a nickel catalyst that has been chemically reduced with hydrogen to an active state can be used as a hydrogenation catalyst. Commercial examples of supported nickel hydrogenation catalysts include those available under the trade names "Nysofact," "Nysosel," and "NI 5248 D" (ex Engelhard Corporation). Other supported nickel hydrogenation catalysts include those commercially available under the trade names "Pricat 9910," "Pricat 9920," "Pricat 9908" and "Pricat 9936" (ex Johnson Matthey).

The metal catalysts may be used as fine dispersions in a hydrogenation reaction (slurry phase environment). For example, in some embodiments, the particles of supported nickel catalyst are dispersed in a protective medium comprising hardened triacylglyceride, edible oil, or tallow. The supported nickel catalyst may be dispersed in the protective medium at a level of about 22 wt % nickel.

The hydrogenation catalysts may be impregnated on solid supports. Some useful supports include carbon, silica, alumina, magnesia, titania and zirconia. Examples of supported catalysts include palladium, platinum, rhodium or ruthenium on carbon or alumina support; nickel on magnesia, alumina or zirconia support; palladium on barium sulphate support; or copper on silica support.

The hydrogenation catalysts may be supported nickel or sponge nickel type catalysts. In some embodiments, the catalyst comprises nickel that has been chemically reduced with hydrogen to an active state (i.e. reduced nickel) provided on a support. The support may comprise porous silica (e.g. kieselguhr, infusorial, diatomaceous, or siliceous earth) or alumina. These catalysts can be characterized by a high nickel surface area per gram of nickel.

The supported nickel catalysts may be of the type described in U.S. Pat. No. 3,351,566, which comprise solid nickel-silica having a stabilized high nickel surface area of preferably 45 to 60 square meters per gram and a total surface area of 225 to 300 square meters per gram. These catalysts can be prepared by precipitating the nickel and silicate ions from solution such as nickel hydrosilicate onto porous silica particles in such proportions that the activated catalyst preferably comprises 25 to 50 wt % nickel and a total silica content of 30 to 90 wt %. The particles can be activated by calcining in air, e.g. at about 300° C. to about 500° C., and then reducing with hydrogen.

Useful catalysts having a high nickel content are described in EP-0168091, wherein the catalyst is made by precipitation of a nickel compound. A soluble aluminum compound is added to the slurry of the precipitated nickel compound while the precipitate is maturing. After reduction of the resultant catalyst precursor, the reduced catalyst typically has a nickel surface area of the order of 90 to 150 square meters per gram of total nickel. The catalysts preferably have a nickel/aluminum atomic ratio in the range of 2 to 10 and a total nickel content of more than about 66% by weight.

Useful high activity nickel/alumina/silica catalysts are described in EP-0167201. The reduced catalysts have a high nickel surface area per gram of total nickel in the catalyst.

Useful nickel/silica catalysts are described in U.S. Pat. No. 6,846,772. The catalysts are produced by heating a slurry of particulate silica (e.g. kieselguhr) in an aqueous nickel amine carbonate solution for a total period of at least 200 minutes at a pH above 7.5, followed by filtration, washing, drying, and optionally calcination. The nickel/silica hydrogenation catalysts are reported to have improved filtration properties. U.S. Pat. No. 4,490,480 describes high surface area nickel/alumina hydrogenation catalysts, preferably having a total nickel content of 5% to 40% by weight.

The hydrogenation catalyst is suitably used at a concentration of less than 10%, preferably less than 5%, more preferably less than 3%, particularly in the range from 0.5 to 2%, and especially 0.8 to 1.2% by weight based on the weight of starting material.

The yield of branched $C_{10}$-$C_{26}$ fatty acids or esters thereof produced according to the process of the present invention is suitably greater than 65%, preferably greater than 70%, more preferably in the range from 75 to 98%, particularly 80 to 95%, and especially 85 to 90% by weight.

The yield of monobranched $C_{10}$-$C_{26}$ fatty acids or esters thereof produced according to the present invention is suitably greater than 60%, preferably greater than 65%, more preferably in the range from 70 to 95%, particularly 75 to 90%, and especially 80 to 85% by weight.

A composition produced according to the process of the present invention suitably comprises (i) greater than 60%, preferably greater than 65%, more preferably greater than 70%, particularly in the range from 73 to 85%, and especially 75 to 80% by weight of $C_{10}$-$C_{26}$ monobranched, preferably saturated, fatty acids, and/or (ii) less than 10%, preferably less than 8%, more preferably less than 6%, particularly in the range from 2 to 5%, and especially 3 to 4% by weight of $C_{10}$-$C_{26}$ polybranched, preferably saturated, fatty acids, both based upon the total weight of the composition. Preferably the process and/or use of the invention produces a composition which comprises greater than 65%, more preferably greater than 70% by weight of $C_{10}$-$C_{26}$ monobranched fatty acids, and/or less than 8%, more preferably less than 6% by weight of $C_{10}$-$C_{26}$ polybranched fatty acids, both based upon the total weight of the composition.

The ratio by weight of monobranched fatty acids to polybranched fatty acids in the composition is (i) suitably greater than 8, preferably greater than 10, more preferably greater than 12, particularly greater than 14, and especially greater than 16, and/or (ii) suitably less than 100, preferably less than 50, more preferably less than 40, particularly less than 30, and especially less than 20. Preferably, the process and/or use of the invention produces a composition in which the ratio by weight of $C_{10}$-$C_{26}$ monobranched fatty acids or alkyl esters thereof to $C_{10}$-$C_{26}$ polybranched fatty acids or alkyl esters thereof is greater than 12, more preferably greater than 14.

The composition preferably also comprises (i) less than 20%, more preferably less than 15%, particularly less than 10%, and especially less than 8% by weight of linear fatty acids; and/or (ii) greater than 2%, more preferably greater than 3%, particularly greater than 4%, and especially greater than 5% by weight of linear fatty acids, both based upon the total weight of the composition.

The concentration of lactones (branched and/or linear) in the composition is suitably less than 5%, preferably less than 3%, more preferably less than 2%, particularly in the range from 0.05 to 1.5%, and especially 0.1 to 1% by weigh, based upon the total weight of the composition.

Preferably, the process and/or use of the invention produce a composition which comprises less than 20% by weight of linear fatty acids and/or less than 3% by weight of lactones, both based upon the total weight of the composition.

The composition preferably (i) has an acid value (measured as described herein) in the range from 145 to 210, more preferably 160 to 205, particularly 175 to 200, and especially 185 to 195 mgKOH/g, and/or (ii) a saponification value (measured as described herein) in the range from 165 to 220, more preferably 175 to 210, particularly 185 to 200, and especially 190 to 195 mgKOH/g, and/or (iii) has an unsaponifiable content (measured as described herein) of less than 10, more preferably less than 5, particularly in the range from 1.0 to 3, and especially 1.5 to 2 g/100 g, and/or (iv) an iodine value (measured as described herein) of less than 3, more preferably less than 1, particularly in the range from 0.05 to 0.5, and especially 0.1 to 0.2 g iodine/100 g, and/or (v) has a cloud point (measured as described herein)

in the range from 15 to 35° C., more preferably 20 to 30° C., particularly 25 to 28° C., and especially 26 to 27° C., and/or (vi) has a solidification point (measured as described herein) in the range from 20 to 35° C., more preferably 25 to 32° C., particularly 27 to 30° C., and especially 28 to 29° C., and/or (vii) a colour (measured as described herein) of less than 100, more preferably less than 50, particularly less than 40, and especially less than 25 Hazen units.

A particular surprising feature of the present invention is that the above defined composition can be obtained by process steps comprising or consisting of (i) isomerisation, (ii) separation of isomerisation catalyst, and optional reuse of the zeolite, (iii) removal of polymeric fatty acids, (iv) hydrogenation, and (v) separation of hydrogenation catalyst. The above order of the aforementioned steps is preferred, but may be varied.

The invention is illustrated by the following non-limiting examples.

In this specification the following test methods have been used.

(i) Acid Value

The acid value was measured using the A.O.C.S. Official method Te 1a-64 (Reapproved 1997), and expressed as the number of milligrams of potassium hydroxide required to neutralise the free fatty acids in one gram of sample.

(ii) Saponification Value

The saponification value was determined using the A.O.C.S. Official Method TI 1a-64 (1997) and is defined as the number of milligrams of potassium hydroxide which reacts with one gram of sample under the prescribed conditions.

(iii) Unsaponifiable Value

The unsaponifiable value was measured using the A.O.C.S. Official Method, Ca6b-53 (1989).

(iv) Iodine Value

The iodine value was determined by the Wijs method (A.O.C.S. Official Method Tg 1-64 (1993)) and expressed as the number of grams of iodine absorbed by 100 grams of sample under the defined test conditions.

(v) Cloud Point

The cloud point was measured according to the A.O.C.S. Official Method (Cc 6-25).

(vi) Solidification Point

The solidification point was measured according to the A.O.C.S. Official Method (Cc 12-59).

(vii) Colour

Colour was determined using the Method of Colour Determination in Hazen Units (Pt—Co scale), ISO 2211 (1973).

(viii) Fatty Acid Composition

The fatty acid composition (chain length, saturated/unsaturated, linear/branched) was determined using gas chromatography, using the method ISO 5508:1990(E) Animal and vegetable fats and oils—Analysis by gas chromatography of methyl esters of fatty acids.

(ix) Zeolite Activity i) 1000 g high oleic sunflower fatty acid, 50 g fresh or regenerated zeolite and 10 g water were charged to a 1.8 liter autoclave. The reaction mixture was flushed 3 times with nitrogen and pressurized with nitrogen to 1 bar. The reaction mixture was heated to 260° C. After 4 hours the reaction mixture was cooled to 80° C. and filtered using filter paper. The resultant filtrate was analysed after microhydrogenation and the degree of conversion measured.

ii) The procedure in i) was repeated except that zeolite recovered from the first reaction mixture by filtration was used. This used zeolite could be used alone or with a certain amount, e.g. 20% by weight of total zeolite, of additional fresh or regenerated zeolite. The time of reaction was 5 hours.

iii) The procedure in ii) was repeated except that zeolite recovered from the reaction mixture in ii) was used and the time of reaction was 6 hours.

iv) The procedure in iii) was repeated, except that zeolite recovered from the reaction mixture in iii) was used, for a total of y hours until the same rate of conversion (same % by weight of unsaturated fatty acid starting material that is reacted) as in iii) was achieved. The % retention of zeolite activity=6/y×100.

v) The procedure in iv) was further repeated a number of times using zeolite recovered from the previous step.

EXAMPLES

Example 1

1000 g of a partially hydrogenated olive oil comprising 2.6% C16:0, 2.6% C18:0, 81.6% C18:1 and 8.8% C18:2, 50 g H-Ferrierite (CP914C (ex Zeolyst), calcined at 500° C. in air) and 10 g water were charged to a 1.8 liter autoclave. The reaction mixture was flushed 3 times with nitrogen and pressurized with nitrogen to 1 bar. The reaction mixture was heated to 260° C. After 5.5 hours, the reaction mixture was cooled to 80° C. and filtered using filter paper. The resultant filtrate was analysed and had the following composition;

| Component | % by Weight* |
|---|---|
| C14 branched | 0.5 |
| C16 branched | 0.6 |
| C18 poly branched | 4.5 |
| C18 mono branched | 58.7 |
| C20 branched | 2.1 |
| C22 branched | 0.1 |
| Linear C16 | 3.0 |
| Linear C18 | 10.0 |
| Lactones (branched + linear) | 6.2 |
| Decarboxylated Dimer | 1.3 |
| Dimer | 9.9 |
| Trimer | 1.3 |

*analysed after microhydrogenation.

The reaction product was then vacuum distilled to 230° C. to remove the dimer/trimer fraction.

Example 2

1000 g high oleic sunflower fatty acid, 25 g H-Ferrierite (CP914C (ex Zeolyst), calcined at 500° C. in air) and 6.8 g water were charged to a 1.8 liter autoclave. The reaction mixture was flushed 3 times with nitrogen and pressurized with nitrogen to 1 bar. The reaction mixture was heated to 260° C. After 6 hours, the reaction mixture was cooled to 80° C. and filtered using filter paper. The resultant filtrate was analysed and had the following composition;

| Component | % by Weight* |
|---|---|
| C14 branched | 0.5 |
| C16 branched | 0.1 |
| C18 poly branched | 4.3 |
| C18 mono branched | 65.1 |
| C20 branched | 1.7 |

-continued

| Component | % by Weight* |
|---|---|
| C22 branched | 0.1 |
| Linear C16 | 1.7 |
| Linear C18 | 11.0 |
| Linear C20 | 0.2 |
| C18:1 | 0.2 |
| Lactones (branched + linear) | 6.3 |
| Decarboxylated Dimer | 0.6 |
| Dimer | 7.0 |
| Trimer | 0.6 |

*analysed after microhydrogenation.

The reaction product was then vacuum distilled to 230° C. to remove the dimer/trimer fraction.

Example 3

565 g of distilled product from Example 1 and 8.6 g hydrogenation catalyst were charged to a 2 liter autoclave. The reaction mixture was flushed 3 times with nitrogen and pressurized with hydrogen to 25 bar. The reaction mixture was heated to 230° C. After 10 hours the reaction mixture was cooled to 80° C. and optionally filtered through a silica gel column. The resultant filtrate was analysed and had the following composition;

| Component | % by Weight |
|---|---|
| C14 branched | 1.0 |
| C16 branched | 0.8 |
| C18 poly branched | 6.0 |
| C18 mono branched | 70.2 |
| C20 branched | 0.2 |
| C22 branched | 0.4 |
| Linear C16 | 3.8 |
| Linear C18 | 14.9 |

Example 4

1000 g erucic fatty acid, 50 g H-Ferrierite (CP914C (ex Zeolyst), calcined at 500° C. in air) and 10 g water were charged to a 1.8 liter autoclave. The reaction mixture was flushed 3 times with nitrogen and pressurized with nitrogen to 1 bar. The reaction mixture was heated to 260° C. After 6 hours, the reaction mixture was cooled to 80° C. and filtered over a carton depth filter. The resultant filtrate was vacuum distilled to 230° C. to remove the dimer/trimer fraction, analysed and had the following composition;

| Component | % by Weight* |
|---|---|
| C16 branched | 0.5 |
| C18 branched | 0.4 |
| C20 branched | 6.4 |
| C22 poly branched | 3.2 |
| C22 mono branched | 66.1 |
| C24 branched | 2.1 |
| Linear C18 | 0.1 |
| Linear C20 | 1.9 |
| Linear C22 | 11.6 |
| Lactones (branched + linear) | 6.7 |

*analysed after microhydrogenation.

Example 5

500 g of the product from Example 4 and 8.6 g hydrogenation catalyst were charged to a 2 liter autoclave. The reaction mixture was flushed 3 times with nitrogen and pressurized with hydrogen to 25 bar. The reaction mixture was heated to 230° C. After 10 hours, the reaction mixture was cooled to 80° C. and optionally filtered through a silica gel column. The resultant filtrate was analysed and had the following composition;

| Component | % by Weight |
|---|---|
| C16 branched | 0.5 |
| C18 branched | 1.0 |
| C20 branched | 7.4 |
| C22 poly branched | 3.7 |
| C22 mono branched | 69.1 |
| C24 branched | 1.5 |
| Linear C16 | 0.4 |
| Linear C18 | 0.4 |
| Linear C20 | 2.3 |
| Linear C22 | 12.7 |

Example 6 i) 1000 g high oleic sunflower fatty acid, 15 g H-Ferrierite and 10 g water were charged to a 1.8 liter autoclave. The reaction mixture was flushed 3 times with nitrogen and pressurized with nitrogen to 1 bar. The reaction mixture was heated to 260° C. After 4 hours the reaction mixture was cooled to 80° C. and filtered using filter paper.

ii) The procedure in i) was repeated except that 12 g H-Ferrierite recovered from the first reaction mixture by filtration and 3 g fresh H-Ferrierite were used. The time of reaction was 5 hours.

iii) The procedure in ii) was repeated except that 12 g H-Ferrierite recovered from the second reaction mixture by filtration and 3 g fresh H-Ferrierite were used. The time of reaction was 7 hours.

iv) The procedure in iii) was repeated several times using H-Ferrierite recovered from the previous reaction mixture. The time of reaction in each case was 6 hours.

The resultant filtrates were analysed and the degree of conversion measured.

| | Fresh Catalyst | 1st reuse | 2nd reuse | 4th reuse | 6th reuse | 9th reuse |
|---|---|---|---|---|---|---|
| Time of Reaction | 4 hours | 5 hours | 7 hours | 6 hours | 6 hours | 6 hours |
| Conversion Rate* | 93% | 91% | 93% | 89% | 90% | 87% |

*analysed after microhydrogenation.

The above examples illustrate the improved properties of a process and use according to the present invention.

The invention claimed is:

1. A process for producing monobranched fatty acids or alkyl esters thereof which comprises;
   (i) isomerising unsaturated $C_{10}$-$C_{26}$ fatty acids or alkyl esters thereof in the presence of a catalyst comprising zeolite, wherein a Lewis base is not present as a co-catalyst, wherein the zeolite is a ferrierite, and wherein the isomerisation reaction is carried out at 255° C. to 350° C.,
   (ii) optionally removing polymeric fatty acids, (iii) optionally hydrogenating the reaction product of step (i) or (ii), and (iv) obtaining a composition from the reaction product of step (i),(ii) or (iii) having a ratio by weight of $C_{10}$-$C_{26}$ monobranched fatty acids or alkyl esters thereof to $C_{10}$-$C_{26}$ polybranched fatty acids or alkyl esters thereof of greater than 6 and less than 100.

2. A process for producing monobranched fatty acids or alkyl esters thereof which comprises;

A) (i) isomerising unsaturated $C_{10}$-$C_{26}$ fatty acids or alkyl esters thereof in the presence of a catalyst comprising zeolite, wherein a Lewis base is not present as a co-catalyst, wherein the zeolite is a ferrierite, and wherein the isomerisation reaction is carried out at 255° C. to 350° C., (ii) separating the reaction product of step (i) from the used zeolite, (iii) optionally removing polymeric fatty acids, (iv) optionally hydrogenating the reaction product of step (ii) or (iii), (v) obtaining a composition from the reaction product of step (ii), (iii) or (iv) having a ratio by weight of $C_{10}$-$C_{26}$ monobranched fatty acids or alkyl esters thereof to $C_{10}$-$C_{26}$ polybranched fatty acids or alkyl esters thereof of greater than 6 and less than 100, and (B) wherein the process steps (A)(i) to (v) are repeated more than once using zeolite comprising used zeolite which has been obtained from step (A)(ii) of the previous reaction cycle.

3. The process according to claim 1 wherein the isomerisation catalyst consists of zeolite.

4. The process according to claim 1 wherein the ratio by weight of $C_{10}$-$C_{26}$ monobranched fatty acids or alkyl esters thereof to $C_{10}$-$C_{26}$ polybranched fatty acids or alkyl esters thereof is greater than 12.

5. The process according to claim 1 wherein the ratio by weight of $C_{10}$-$C_{26}$ monobranched fatty acids or alkyl esters thereof to $C_{10}$-$C_{26}$ polybranched fatty acids or alkyl esters thereof is greater than 14.

6. The process according to claim 1 wherein the composition comprises greater than 65% by weight of $C_{10}$-$C_{26}$ monobranched fatty acids, and/or less than 8% by weight of $C_{10}$-$C_{26}$ polybranched fatty acids, both based upon the total weight of the composition.

7. The process according to claim 6 wherein the composition comprises greater than 70% by weight of $C_{10}$-$C_{26}$ monobranched fatty acids, and/or less than 6% by weight of $C_{10}$-$C_{26}$ polybranched fatty acids, both based upon the total weight of the composition.

8. The process according to claim 1 wherein the composition comprises less than 20% by weight of linear fatty acids and/or less than 3% by weight of lactones, both based upon the total weight of the composition.

9. The process according to claim 2 wherein step (B), in which the zeolite is reused, occurs 3 or more times.

10. The process according to claim 2 wherein the used zeolite catalyst retains at least 90% of its activity.

11. The process according to claim 10 wherein the used zeolite catalyst retains at least 95% of its activity.

12. A steady state process comprising: isomerising unsaturated $C_{10}$-$C_{26}$ fatty acids or alkyl esters in the presence of a zeolite catalyst to produce a composition having a ratio by weight of $C_{10}$-$C_{26}$ monobranched fatty acids Or alkyl esters thereof to $C_{10}$-$C_{26}$ polybranched fatty acids or alkyl esters thereof of greater than 6 and less than 100, wherein the zeolite catalyst is a ferrierite, and wherein the isomerisation reaction is carried out at 255° C. to 350° C., wherein a Lewis base is not present as a co-catalyst; and separating the zeolite catalyst from the produced composition, wherein the steady state process is performed continuously.

13. A composition produced by the process according to claim 1.

14. A composition produced by the process according to claim 2.

15. The process according to claim 1 wherein a Lewis base is not present in the isomerisation step (i).

16. The process according to claim 2 wherein a Lewis base is not present in the isomerisation step (A)(i).

* * * * *